United States Patent [19]

Sobel et al.

[11] Patent Number: 4,861,710

[45] Date of Patent: Aug. 29, 1989

[54] RECOMBINANT DNA CLONE ENCODING LAMININ RECEPTOR

[75] Inventors: Mark E. Sobel, Bethesda; Lance A. Liotta, Potomac; Ulla M. Wewer, Rockville, all of Md.; Michael C. Jaye, Arlington; William N. Drohan, Springfield, both of Va.

[73] Assignee: The United States of America as represented by the Department of Health and Human Services, Washington, D.C.

[21] Appl. No.: 911,863

[22] Filed: Sep. 26, 1986

[51] Int. Cl.$^4$ .................. C12Q 1/68; C07H 21/00; C12N 1/19; C12N 1/185

[52] U.S. Cl. ........................... 435/6; 536/27; 436/813; 436/63; 935/78; 935/9; 435/252.8

[58] Field of Search ............... 536/27; 435/6, 803, 435/253, 320, 252.8; 935/78, 9; 436/501, 813, 63; 530/395

[56] References Cited

U.S. PATENT DOCUMENTS

| | | | |
|---|---|---|---|
| 4,565,789 | 1/1986 | Liotta et al. | 530/387 X |
| 4,589,881 | 5/1986 | Pierschbacher et al. | |
| 4,628,027 | 12/1986 | Gay | 436/506 X |
| 4,699,877 | 10/1987 | Cline et al. | 436/813 X |

OTHER PUBLICATIONS

Leptin, M., Nature, vol. 321, 19 Jun. 1986, p. 728.
Suzuki et al., 1985, The EMBO Journal 4:2519–2524, "Complete Amino Acid Sequence of Human Vitronectin Deduced from cDNA, Similarity of Cell Attachment Sites in Vitronectin and Fibronectin".
Pytela et al., 1985, Proc. Natl. Acad. Sci. U.S.A. 82:5766–5770, "A 125/115–kDa Cell Surface Receptor Specific for Vitronectin Ineracts with the Arginine–Glycine–Aspartic Acid Adhesion Sequence Derived from Fibronectin".
Krotoski et al., 1986, J. Cell Bio 103:1061–1071, "Distribution of a Putative Cell Surface Receptor for Fibronectin and Laminin in the Avian Embryo".
Pytela et al., 1985, Cell 40:191–198, "Identification and Isolation of a 140 kd Cell Surface Glycoprotein with Properties Expected of a Fibronectin Receptor".
Horwitz et al., 1985, J. Cell Bio. 101:2134–2144, "The Cell Substrate Attachment (CSAT) Antigen Has Properties of a Receptor for Laminin and Fibronectin".
Rao et al., 1983, Biochem. Biophys. Research Commu. 111:804–809, "Isolation of a Tumor Cell Laminin Receptor".
Lesot et al., 1983, The EMBO Journal 2:861–865, "Isolation of a Laminin-Binding Protein from Muscle Cell Membranes".
Malinoff et al., 1983, J. Cell. Bio. 96:1475–1479, "Isolation of a Cell Surface Receptor Protein for Laminin from Murine Fibrosarcoma Cells".
Terranova et al., 1983, Proc. Natl. Acad. Sci. U.S.A. 80:444–448, "Laminin Receptor on Human Breast Carcinoma Cells".
Liotta et al., 1985, Exp. Cell Res. 156:117–126, "Monoclonal Antibodies to the Human Laminin Receptor Recognize Structurally Distinct Sites".
Togo et al., Basement Membranes 1985, pp. 325–332, "Monoclonal Antibodies to the Human Laminin Receptor Inhibit Cell Attachment to Native Human Basement Membranes".
Barsky et al., 1984, J. Clin. Invest. 74:843–848, "Laminin Molecular Domains with Alter Metastasis in a Murine Model".
Hand et al., 1985, Cancer Research 45:2713–2719, "Expression of Laminin Receptor in Normal and Carcinomatous Human Tissues as Defined by a Monoclonal Antibody".
Young et al., 1983, Proc. Natl. Acad. Sci. U.S.A. 80: 1194–1198, "Efficient Isolation of Genes by Using Antibody Probes".
Young et al., 1983, Science 222: 778–782, "Yeast RNA Polymerase II Genes: Isolation with Antibody Probes".

Primary Examiner—Johnnie R. Brown
Assistant Examiner—Jeremy M. Jay
Attorney, Agent, or Firm—Fleit, Jacobson, Cohn, Price, Holman & Stern

[57] ABSTRACT

The invention provides a recombinant cDNA clone encoding cell surface receptor for laminin, as well as a probe and methods of using that probe to diagnose the aggressiveness of a carcinoma or the effectiveness of an agent for treating cancer cells.

19 Claims, 8 Drawing Sheets

FIG. 6

```
                                                                                                                      60
GAA  TTC      GCT  CGT  GAT  GGC  ATC  TAT  ATC  ATA  AAT  CTC  AAG  AGG  ACC  TGG  GAC  AAG  CTT  CTG
     EcoRI    ala  arg  asp  gly  ile  tyr  ile  ile  asn  leu  lys  arg  thr  trp  glu  lys  leu  leu
                                                                                                                     120
GCA  GCT      CGT  GCA  ACT  ATT  GAA  GCC  GTT  CCT  TCC  AGG  GAT  GCC  AGT  ACT  CCT  TCC  TTC  AGG
ala  ala      arg  ala  thr  ile  glu  ala  val  pro  ser  arg  asp  ala  ser  thr  pro  ser  phe  arg
                                                                                                                     180
AAT  CGC      GGC  CAG  AGG  CCT  ACT  CTG  GAA  ACC  GGA  CCC  GTG  ACT  GCC  GGA  CCA  CCA  CCA  GCT
asn  arg      gly  gln  arg  pro  thr  leu  glu  thr  gly  pro  val  thr  ala  gly  pro  pro  pro  ala
                                                                                                                     240
GGC  CCT      TTC  ACT  GGA  ACT  GGA  ATC  AAC  AAC  AAG  CAG  TTC  ATG  AGG  CCC  GAG  AAG  CCA  CCA
gly  pro      phe  thr  gly  thr  gly  ile  asn  asn  lys  gln  phe  met  arg  pro  glu  lys  pro  pro
                                                                                                                     300
CTT  GTG      CCT  ACT  ATT  AAC  CAC  CAG  CAC  GAT  GTG  CCT  CAC  GAA  AAA  CAG  GCA  TCT  CGC  CGG
leu  val      pro  thr  ile  asn  his  gln  his  asp  val  pro  his  glu  lys  gln  ala  ser  arg  arg
                                                                                                                     360
AAC  CTA      TGC  AAC  AAC  GCA  CAG  GCT  TCA  TCC  ATT  GAG  CAC  GGT  GAA  AAA  CTA  AAC  GGA  GAT
asn  leu      cys  asn  asn  ala  gln  ala  ser  ser  ile  glu  his  gly  glu  lys  leu  asn  gly  asp
                                                                                                                     420
ATC  CCA      CTC  ACC  AAG  CGC  CAT  GAG  TAT  TGG  CGA  GAT  GTA  GAT  GCA  GAT  TCT  GGT  CTA  CGC
ile  pro      leu  thr  lys  arg  his  glu  tyr  trp  arg  asp  val  asp  ala  asp  ser  gly  leu  arg
                                                                                                                     480
GAA  GTT      TGC  CTC  ATC  GAA  ATT  CAC  ATT  GTG  CAC  GAG  AAA  GCT  TCT  GGT  TCA  CCG  ATG  GCC
glu  val      cys  leu  ile  glu  ile  his  ile  val  his  glu  lys  ala  ser  gly  ser  pro  met  ala
                                                                                                                     540
CTC  TAC      TTC  ACC  ATG  AGA  GAG  GAT  CAG  GAA  CAG  GAA  GCA  GAG  ATG  CCA  TGG  GAG  GCA  CGG
leu  tyr      phe  thr  met  arg  glu  asp  gln  glu  gln  glu  ala  glu  met  pro  trp  glu  ala  arg
                                                                                                                     600
GCA  GTC      ACC  CCT  TAC  AAG  GAT  GAA  AAA  GCC  GCC  GAC  GAG  CCC  GAG  GTG  TCT  TGG  GAC  AAG
ala  val      thr  pro  tyr  lys  asp  glu  lys  ala  ala  asp  glu  pro  glu  val  ser  trp  asp  lys
                                                                                                                     660
ACT  CAG      CCC  CCA  GAC  ATG  GGT  CAG  GCT  ACT  GCC  GGG  CAG  CAC  ACT  GAA  GAC  ATT  GCT  CAG
thr  gln      pro  pro  asp  met  gly  gln  ala  thr  ala  gly  gln  his  thr  glu  asp  ile  ala  gln
                                                                                                                     720
CAA  TTC      CTT  CAC  CAC  GAC  TGG  GGG  GCA  GCC  AGC  ACC  GGT  CGA  GAC  ATT  CCA  GCA  CAA  CCC
gln  phe      leu  his  his  asp  trp  gly  ala  ala  ser  thr  gly  arg  asp  ile  pro  ala  gln  pro
                                                                                                                     780
ACT  GCT      CCT  CAG  CAA  GCA  GGC  GCC  ACT  ACC  ACC  ACA  ACC  AAC  GAT  GCT  GTT  GCT  CCT  GCA
thr  ala      pro  gln  gln  ala  gly  ala  thr  thr  thr  thr  thr  asn  asp  ala  val  ala  pro  ala TAC  CCT      CAC  AAC  CAT  CAT  ATG  AAA  ACA  GGA  TCA  ACA  TAA  TCA  TCT  A(n)
```

1700 —

1  2  3  4

INHIBITION OF LAMININ BINDING TO CELLS

LAMININ RECEPTOR BINDING DOMAIN

RECOMBINANT DNA CLONE ENCODING LAMININ RECEPTOR

BACKGROUND OF THE INVENTION

1. Technical Field

The present invention is related generally to recombinant DNA. More particularly, the present invention is related to a recombinant cDNA clone encoding high affinity (about $10^{-8}$ to $10^{-10}$ Kd) cell surface receptors for laminin.

2. State of the Art

Laminin is a major glycoprotein component of basement membranes and mediates the attachment of both epithelial and neoplastic cells to the basement membrane. The basement membrane is a ubiquitous, specialized type of extracellular matrix separating organ parenchymal cells from interstitial collagenous stroma. Interaction of cells with this matrix is an important aspect of both normal and neoplastic cellular processes. Normal cells appear to require an extracellular matrix for survival, proliferation, and differentiation, while migratory cells, both normal and neoplastic, must traverse the basement membrane in moving from one tissue to another. In particular, metastatic cancer cells arising in squamous or glandular epithelium must traverse the basement membrane in moving from one tissue to another. In particular, metastatic cancer cells arising in squamous or glandular epithelium must traverse the basement membrane to enter the circulatory and lymphatic systems (intravasation); the circulating neoplastic cells are typically arrested in the capillary beds of an organ, invade the blood vessel walls, and penetrate the basement membrane to extravascular tissue (extravasation), where a secondary neoplasm is then established. Laminin receptor, by mediating the attachment of both epithelial and neoplastic cells to the basement membrane, plays a critical role in controlling, inter alia, the metastatic process. U.S. Pat. No. 4,565,789 describes the isolation and characterization of certain aspects of laminin receptor. But a cloned DNA sequence for encoding cell surface receptor for laminin has not heretofore been known.

SUMMARY OF INVENTION

It is, therefore, an object of the present invention to provide a recombinant cDNA clone capable of encoding high affinity (about $10^{-8}$ to $10^{-10}$ Kd) cell surface receptor for laminin.

It is a further object of the present invention to provide synthetic fragment(s) of laminin receptor which inhibit metastases.

It is a still further object of the present invention to provide a method for producing large quantities of synthetic laminin receptor.

It is an additional object of the present invention to provide synthetic fragments of laminin receptor which encode specific domains such as membrane-spanning and ligand binding regions.

It is another object of the present invention to provide a diagnostic method to assess the content of laminin receptor mRNA in different tumor cell and normal tissue cell populations.

It is a still further object of the present invention to provide a diagnostic method to determine the pattern of laminin receptor genes in different tissue and tumor cell populations.

BRIEF DESCRIPTION OF DRAWINGS

These and other objects, features and many of the attendant advantages of the invention will be better understood upon a reading of the following detailed description when considered in connection with the accompanying drawings wherein.

Figure 2:
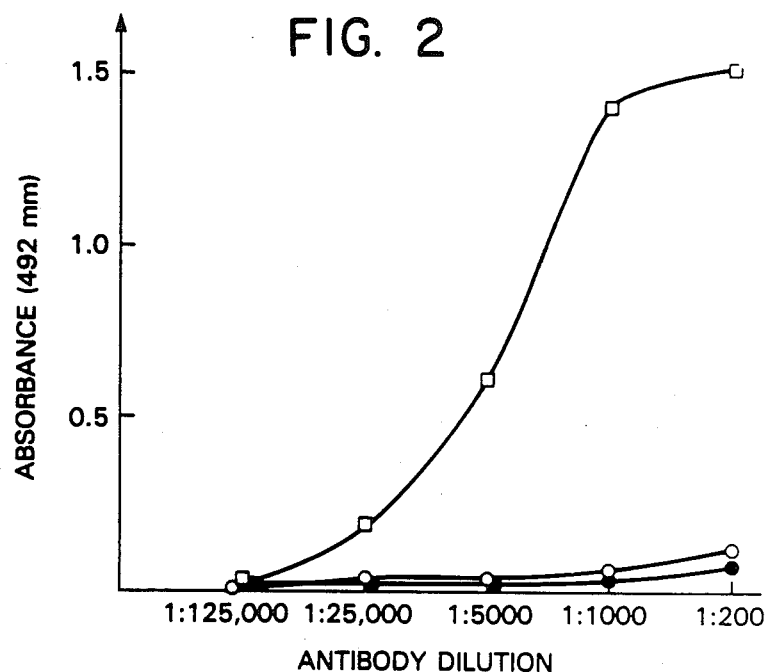
Figure 5:
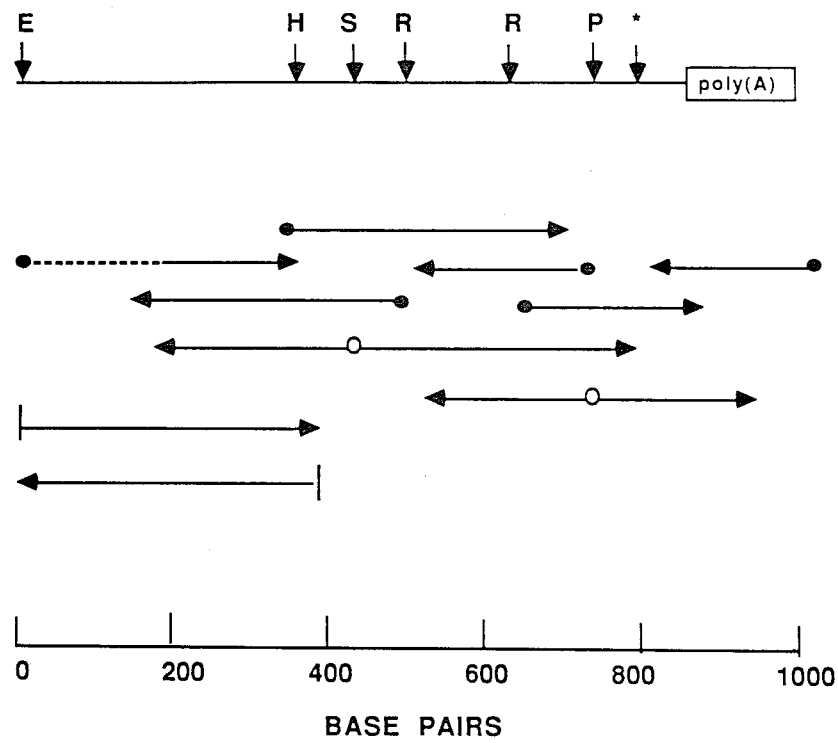
Figure 3:
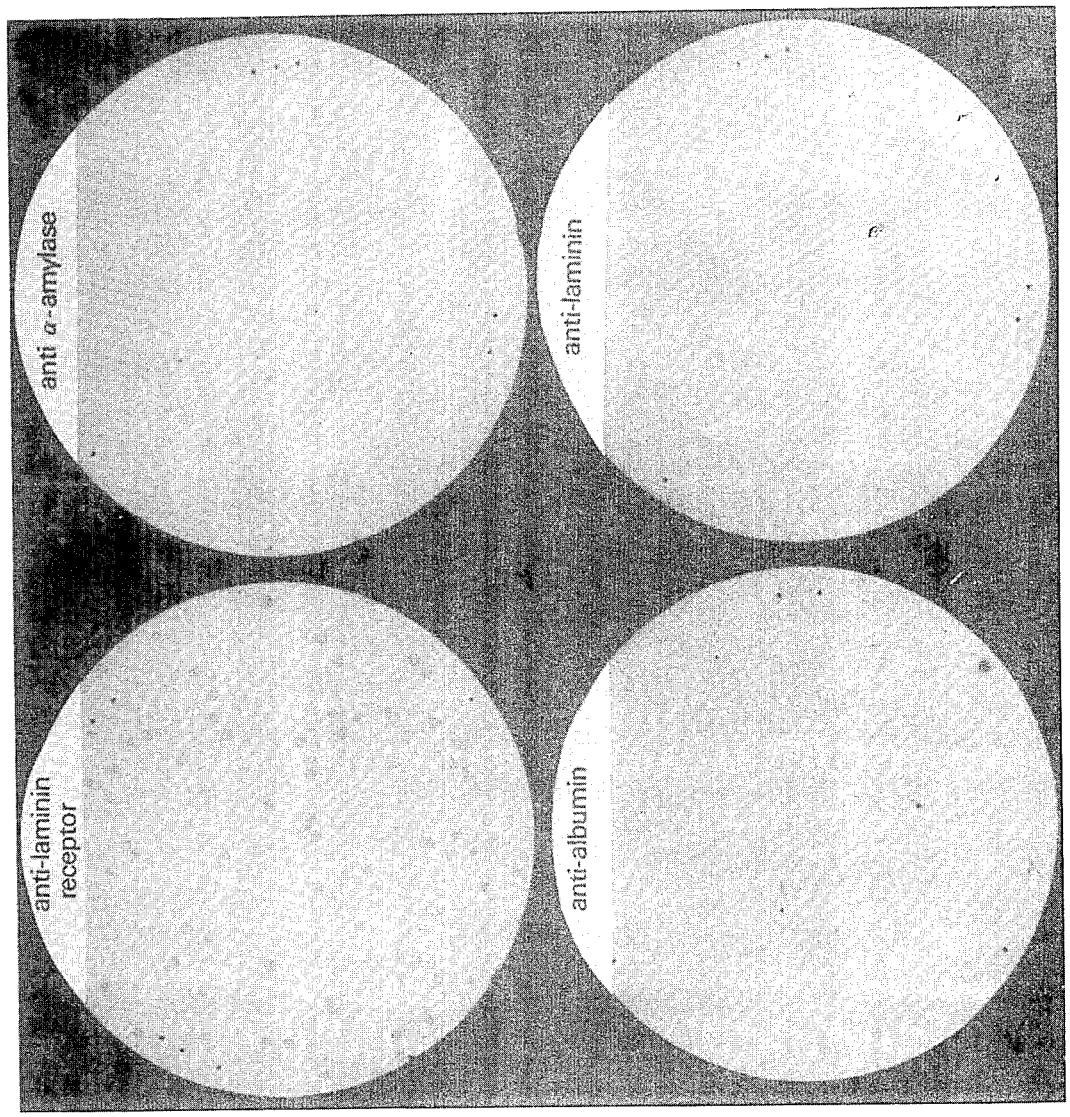
Figure 4:
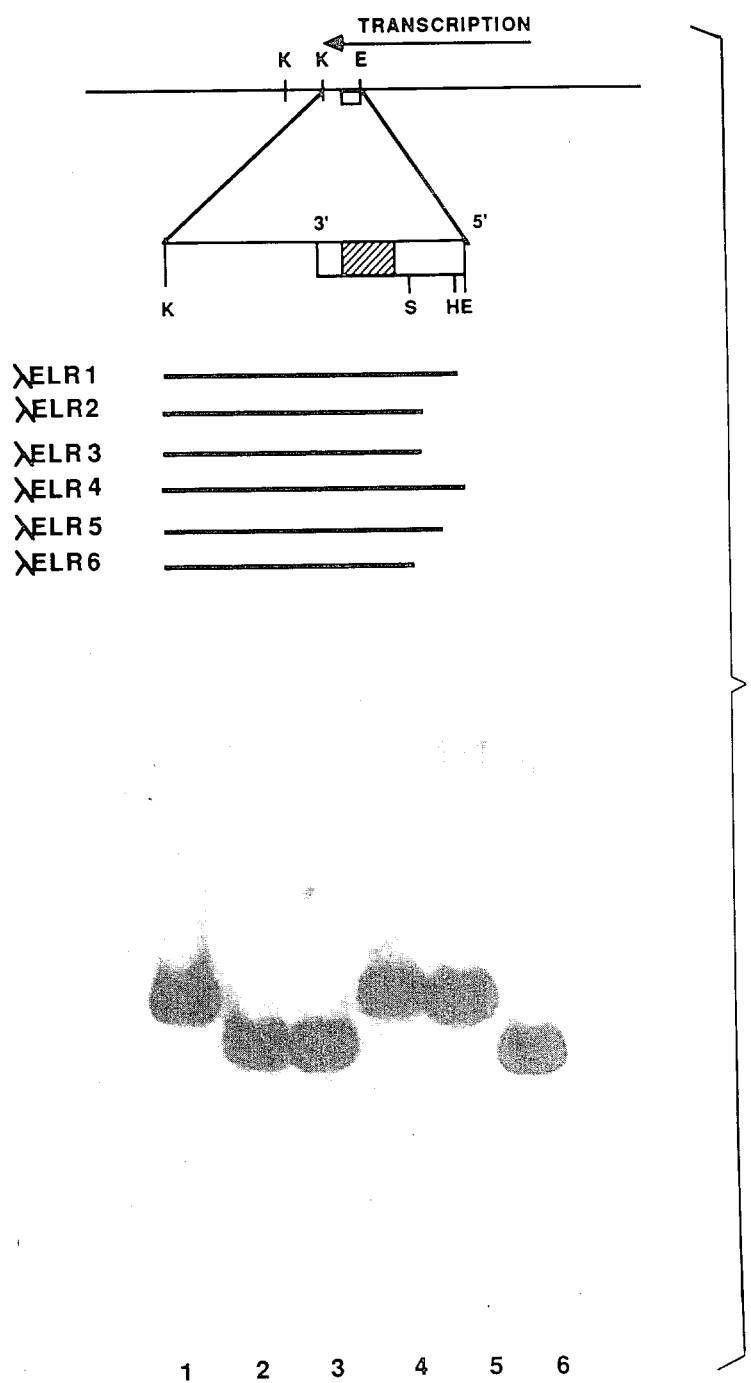
Figure 7:
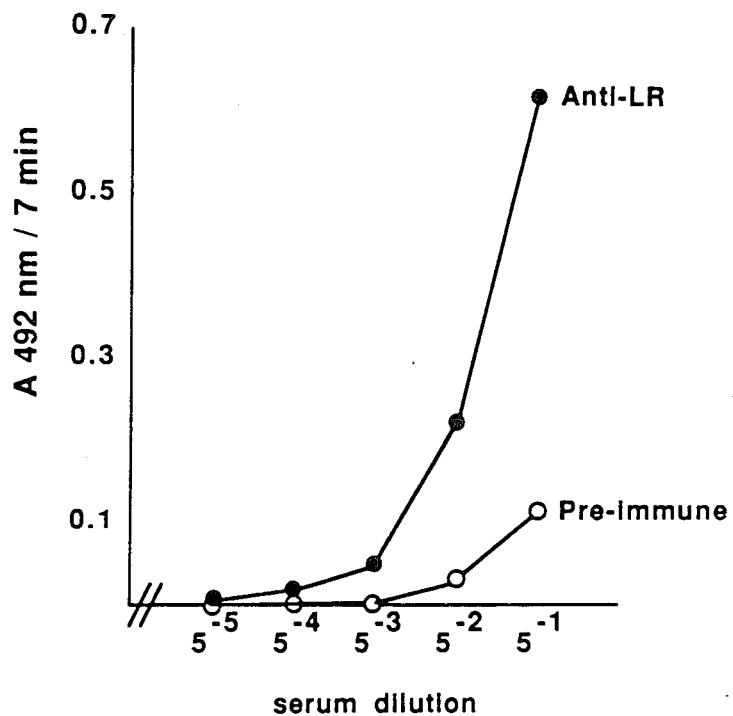
Figure 9:
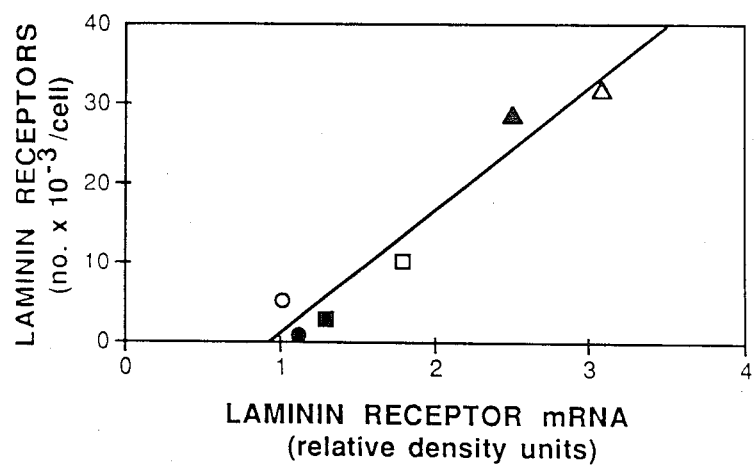
Figure 8:
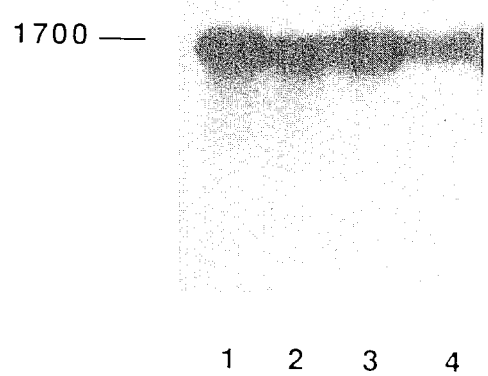
Figure 10:
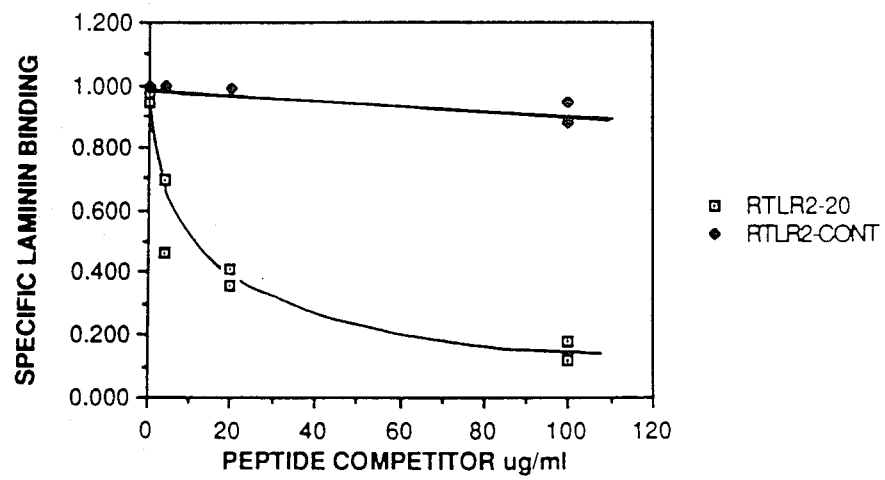
Figure 11:
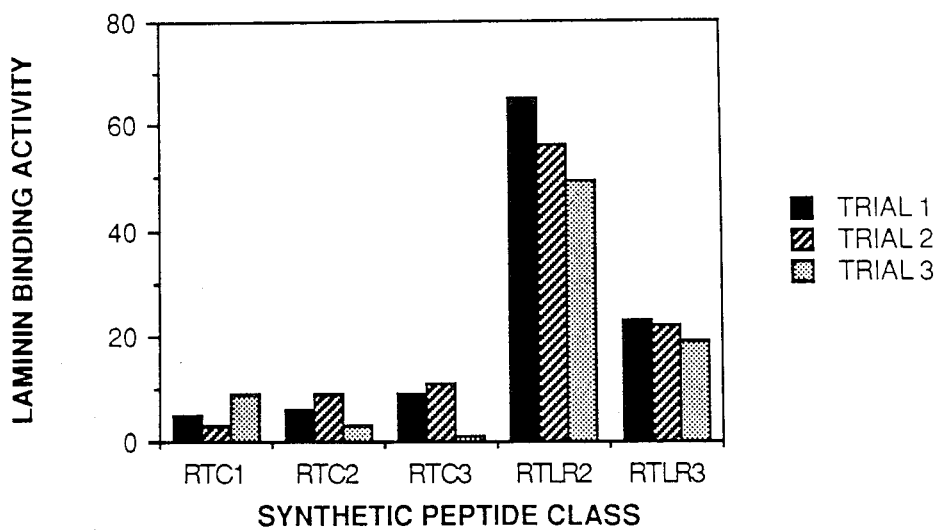

BOTTOM shows isoelectric focusing and two-dimensional gel electrophoresis of the purified laminin receptor. The colon carcinoma laminin receptor protein sample (0.1 µg) shown above was radiolabeled with $I^{125}$ and subjected to isoelectric focusing (pH range 5–7) and two-dimensional gel electrophoresis on a 10% NaDodSO$_4$-polyacrylamide gel. Molecular weight markers: phosphorylase b (93,000), bovine serum albumin (66,000), glyceraldehyde 3-phosphate dehydrogenase (36,000);

FIG. 2 shows an ELISA of the purified laminin receptor. Each microtiter well was coated with purified tumor laminin receptor and reacted for 2 hours against LR1 monoclonal antibody 2H5 (□), anti-albumin (O) or anti-α-amylase monoclonal antibody ( ). Antibodies were detected using peroxidase-conjugated goat anti-mouse IgM or peroxidase-conjugated swine anti-rabbit IgG;

FIG. 3 depicts the specificity of the anti-laminin receptor monoclonal antibody for λELR6 plaques. Filters containing approximately 50–100 purified λELR6 plaques were reacted with either anti-laminin receptor monoclonal antibody, anti-α-amylase monoclonal antibody, anti-albumin antibody or anti-laminin antibody. Antibody binding was detected using peroxidase-conjugated second antibody;

FIG. 4 demonstrates the overlapping laminin receptor cDNA inserts of λELR1-6. The top line is a diagram of a prototype λELR recombinant λgt11 phage, showing the two KpnI sites (K) to the left of the cDNA inserts. The box depicts the cDNA insert. The left EcoRI site in each insert was not present. The right EcoRI site (E) is shown. Transcription from the lacZ gene of λgt11 proceeds from the right arm of the phage toward the left, through E. The region extending from the KpnI site (closest to the cDNA insert) to the EcoRI site of the largest cDNA insert (λELR4) is expanded and shown below. The stippled area in the cDNA insert box designates the PstI-SphI restriction fragment isolated from a subclone of λELR4 (see FIG. 5) which was nick translated and used as a hybridization probe. The common SacI (S) and HindIII (H) sites described in the text are indicated. Phage DNA from each of the λELR recombinant phage was restricted with KpnI and EcoRI, electrophoresed through a 1% agarose gel, transferred to nitrocellulose, and stringently hybridized to the PstI-SphI restriction fragment described above. The length of the KpnI-EcoRI restriction fragment from each of the λELR recombinant phage which hybridized to the probe is diagrammed above the radioautograph of the blot, and was determined by comparison to standard λ/HindIII digests;

FIG. 5 diagrams the strategy to sequence the cDNA insert of λELR4. The restriction map of subcloned insert of λELR4 is shown on top. E is the 5′ EcoRI site of the insert. H: HinfI, S: SphI, R: RsaI, P: PstI, *: ochre termination codon. The arrows indicate the sequencing direction of fragments labeled either by kinasing at the 5′ end with (λ-$P^{32}$) ATP ( ) or by tailing at the 3′ end with (α-$P^{32}$) dideoxy ATP (O) or by the dideoxy synthesis method (γ). Subclones used for sequencing were pLR4-1, pLR4-2, and pLR4-4;

FIG. 6 provides the nucleotide sequence of the λELR cDNA insert with derived protein sequence below. Shown to the right of each line is the number of base pairs from the artificial EcoRI site (bases 1–6);

FIG. 7 shows ELISA determination of synthetic laminin receptor peptide. Synthetic laminin receptor peptide RTLR2 was generated from the cDNA sequence in FIG. 6 and was assayed by ELISA using different dilutions of rabbit anti-laminin receptor antiserum or preimmune serum;

FIG. 8 shows an RNA gel blot hybridization. Total cellular RNA was extracted from several breast carcinoma cell lines, separated on methylmercury agarose gels and transferred to diazobenzyloxymethylcellulose paper. The filter was hybridized to nick translated ($^{32}P$)-labeled EcoRI-PstI insert from pLR4-1. The length of the hybridized mRNA species was determined by comparison with the known sizes of rRNA and with the sizes of λDNA restricted with HindIII. Lane 1: MCF-7 (parent); Lane 2: MCF7-3E5; Lane 3: MCF7-5H7, Lane 4: ZR75;

FIG. 9 shows the correlation of laminin receptor mRNA levels with ability of six human carcinoma cell lines to bind laminin. Different timed exposures of radioautographs such as shown in FIG. 8 were measured densitometrically to determine a linear response range. The lowest amount of RNA hybridized in the series was assigned the number 1.0 and all other values were calculated relative to that value. The number of laminin receptors per cell for each cell line was calculated from Scatchard plots of specifically bound ($I^{125}$) laminin to log growth phase cells. A linear regression analysis revealed a correlation coefficient of 0.97. MCF-7 parent □, MCF-7 Clone 5H7Δ, MCF-7 Clone 3E5( ), ZR-75 0, renal carcinoma A-704 , Panc-1 ;

FIG. 10 demonstrates that synthetic laminin receptor peptide inhibits laminin binding to cells. The ability of A2058 human melanoma cells to bind specifically to laminin was tested in the presence of various amounts of RTLR2 or RTLR2-control fragments generated from the cDNA sequence of FIG. 6. Values are expressed relative to the amount of laminin bound in the absence of added fragment; and FIG. 11 shows identification of synthetic peptide laminin receptor fragments involved in ligand binding. Peptide fragments generated from cDNA sequence with predicted reverse turn conformation (RTLR2, RTLR3) as well as control peptides were bound to glass beads and incubated with ($I^{125}$) laminin. The values shown are the number of cpm×$10^{-3}$ bound to beads after subtraction of cpm bound to beads without fragment.

DETAILED DESCRIPTION OF INVENTION

The above and various other objects and advantages of the present invention are achieved by a recombinant cDNA clone having nucleotide sequence, in whole or in part (as shown in FIG. 6), encoding cell surface laminin receptor and a method for producing synthetic laminin receptor or a fragment thereof.

Unless defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

The methodology for constructing and isolating the recombinant cDNA clone of the present invention is described in further detail in Example II and includes the following general steps, involving standard techniques well known in the art:

(a) cDNA is synthesized using mRNA template from human umbilical vein endothelial cells.

(b) endothelial cell cDNA is inserted into the λgt11 vector (ATCC 37194).

(c) The recombinant λgt11 is packaged and used to infect *Escherichia coli* 1090 cells (ATCC 37197).

(d) The resulting λgt11 human endothelial cell cDNA expression library is screened with a monoclonal antibody which recognizes a domain of the human laminin receptor involved in binding of laminin.

(e) Six plaques, designated λELR1-6, are thus isolated and purified (FIG. 3). The cDNA inserts are analyzed by restriction endonuclease mapping and are found to have a common domain, indicating that they encode the epitope of the laminin receptor recognized by the monoclonal antibody (FIG. 4).

(f) The largest cDNA insert of the six purified phage is subcloned into plasmid vectors to facilitate further analysis and DNA sequencing. The EcoRI site linking the cDNA insert to the left arm of λgt11 is missing in all six clones. A PvuII site 11 bp downstream is therefore utilized to purify cDNA insert from the largest recombinant phage, λELR4. The EcoRI-PvuII restriction fragment of λELR4 is subcloned into the EcoRI-PvuII sites of pBR322 to make pLR4-1.

A deposit of the recombinant cDNA clone pLR4-1 transformed into host *E. coli* strain C600r−m− (ATCC 33525) obtained in accordance with the present invention has been made at the American Type Culture Collection (ATCC), Rockville, Md., under accession number 67199. Upon request, the Commissioner of PTO shall have access to the deposit, and upon issuance of the patent, this deposit will continue to be viably maintained for at least 5 years after the last request or at least 30 years or the life of the patent and made available to the public without restriction, of course, consistent with the provisions of the law.

The method for definitively identifying the present invention was based on comparison of cDNA sequence of the recombinant plasmids (FIG. 6) with the amino acid sequence of a cyanogen bromide-generated octapeptide of purified placental laminin receptor. The methodology for obtaining octapeptide amino acid sequence is described in further detail in EXAMPLE I and includes the following general steps, involving standard techniques well known in the art:

(a) Microsomal membranes from human placental tissue are prepared and solubilized.

(b) The solubilized microsomal membrane-containing preparation is passed through an affinity matrix of purified laminin-Sepharose 4B and after extensive washing, the high affinity laminin receptor protein is eluted from the ligand by high salt (1M NaCl).

Figure 1:
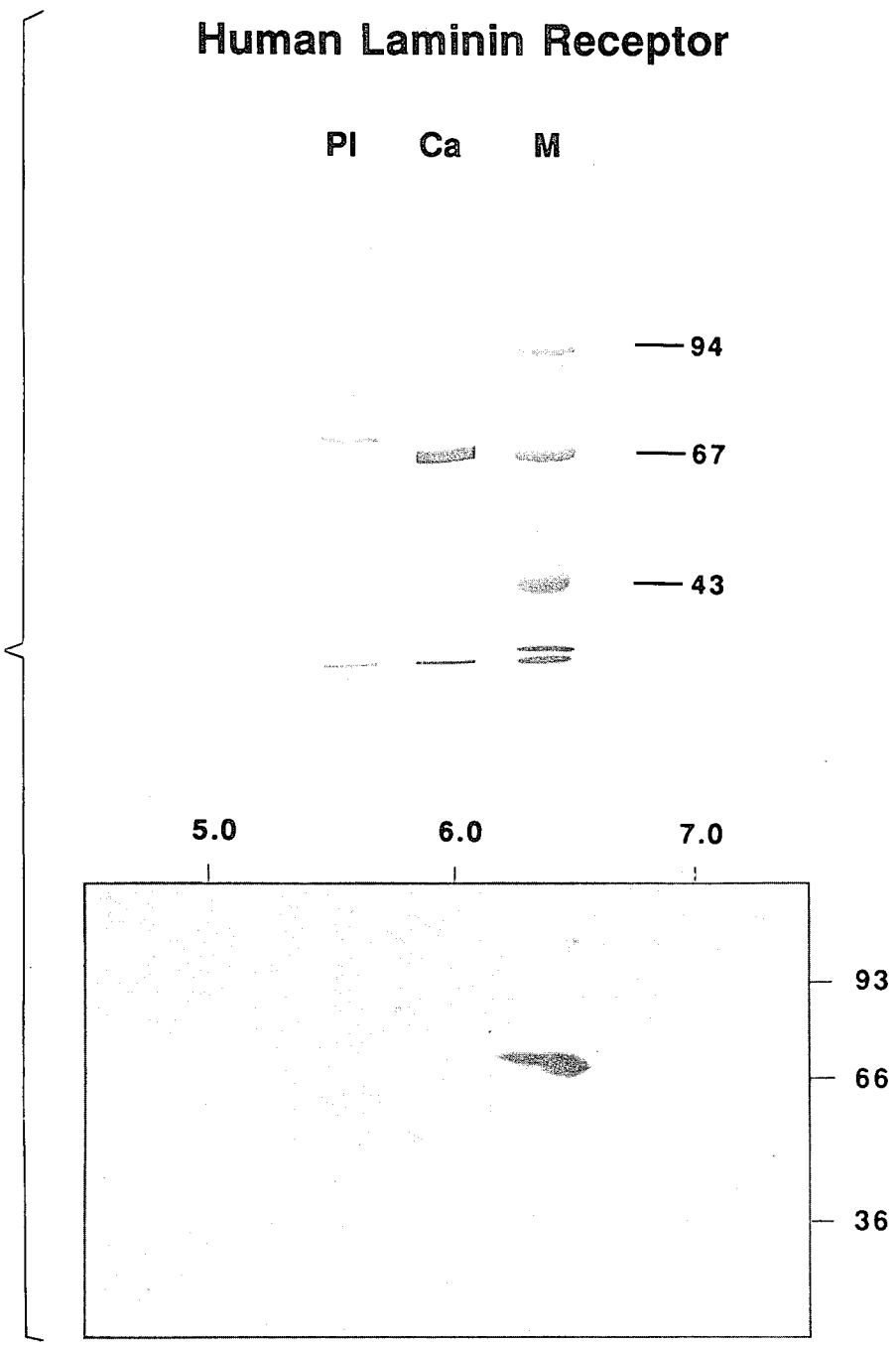
FIG. 1 demonstrates the homogeneity of purified laminin receptor. TOP shows comparison of the purified laminin receptor from colon carcinoma and from normal human placental tissue. Materials eluted with 1M NaCl from the laminin-Sepharose affinity column were analyzed by NaDodSO$_4$-polyacrylamide gel electrophoresis (7%) in the presence of dithiothreitol and visualized with silver staining. The panel exemplifies the slight variability of the molecular weight (68,000–72,000) between preparations of the laminin receptor. Lane Pl: Laminin receptor (1 µg) isolated from human placental tissue. Lane Ca: Laminin receptor (3 µg) isolated from human colon carcinoma. Lane M: Molecular weight markers: phosphorylase b (94,000), bovine serum albumin (67,000), and ovalbumin (43,000).

(c) The homogeneity of the human placental laminin receptor is assayed by two dimensional gel electrophoresis (FIG. 1) and enzyme-linked immunosorbent assay (ELISA) (FIG. 2).

(d) The human placental laminin receptor is cleaved with cyanogen bromide and the resulting peptides are fractionated by reverse phase high pressure liquid chromatography (HPLC).

(e) Microsequence analysis of a placental oligopeptide reveals an octapeptide with the unique sequence Met-Leu-Ala-Arg-Glu-Val-Leu-Arg.

An alternate method for identifying the present invention was based on the ability of rabbit antiserum directed against human metastatic breast carcinoma laminin receptor to identify (by ELISA), a synthetic peptide generated from the cDNA sequence of pLR4-1 (FIG. 7). The methodology for obtaining the anti-laminin receptor antiserum is described in further detail in EXAMPLE IV and includes the following general steps, involving standard techniques well known in the art:

(a) Laminin receptor is purified from human metastatic breast carcinoma as described supra for placental laminin receptor.

(b) Homogeneity of the tumor laminin receptor is assessed as described supra for placental laminin receptor.

(c) Rabbits are immunized by subcutaneous injections of tumor laminin receptor cut out of NaDodSO₄ polyacrylamide gels.

Diagnostic assays for cells containing laminin receptor mRNA, such as human cancer cells, have been developed as useful tools in the diagnosis and prognosis of cancer. The method for assaying laminin receptor mRNA content is described in further detail in EXAMPLE V and includes the following general steps, following standard techniques well known in the art:

(a) Total cellular RNA is isolated from tissue specimen or cells.

(b) RNA is denatured and electrophoresed through denaturing agarose gels and transferred to a filter paper.

(c) The filter paper containing the RNA is hybridized to radiolabeled laminin receptor cDNA.

(d) After washing, the filter is exposed to X-ray film for sufficient time to obtain an image of the radioactive probe.

(e) The relative intensity of the band on the film is a measure of the content of laminin receptor mRNA (FIG. 8).

(f) Alternatively, in lieu of step (b) above, a small aliquot of denatured RNA can be directly bound to filter paper followed by steps (c) thru (e).

(g) Radiolabelled laminin receptor cDNA can also be hybridized in situ to tissue sections and cells to determine specific cell populations expressing laminin receptor mRNA.

Increased content of laminin receptor mRNA in metastatic cells lends to the development of diagnostic assays for cells containing altered laminin receptor DNA. The methodology is based on the possible presence of restriction fragment length polymorphisms as has been found for a variety of genetic diseases. Amplification of laminin receptor genes in the genome of tumor or metastatic cells may also be assessed. The method for analyzing laminin receptor genomic DNA includes the following general steps, following standard techniques well known in the art:

(a) High molecular weight genomic DNA is isolated from tissue specimen or cells, as described in EXAMPLE VI.

(b) DNA is digested with a variety of restriction endonucleases, electrophoresed through agarose gel and transferred to filter paper.

(c) The filter containing the DNA is hybridized to radiolabeled laminin receptor cDNA.

(d) After washing, the filter is exposed to X-ray film and the pattern of bands on the film is compared to that from normal tissue.

Synthetic peptides generated from the cDNA sequence of pLR4-1 are useful in the treatment of cancer to inhibit formation of metastases. The methods described herein are based on the observation that the basement membrane is a continuous structure in benign neoplasms, and that laminin receptors on benign cells are occupied by attachment to basement membrane. In contrast, the basement membrane adjacent to invading tumor cells is not continuous. Invading tumor cells thus may have increased numbers of laminin receptors expressed on the cell surface which are not bound to ligand. It is the availability of laminin receptor sites on metastasizing carcinoma cells which is an important concept in the management and diagnosis of cancer. The aggressiveness of a carcinoma, defined as the tendency for a tumor cell of that carcinoma to migrate out of the primary tumor site into adjacent normal tissue and its propensity for spreading to distant sites in the body to initiate metastatic clones, is, then, in part, a reflection of the number of invasive cells with more available laminin receptors.

Synthetic peptide generated from the cDNA sequence of pLR4-1 bound specifically to radiolabeled laminin (FIG. 11). Presence of the synthetic peptide in laminin binding assays inhibited the ability of cells to bind to laminin (FIG. 10). Thus, synthetic peptide can compete with and block the ability of cell surface laminin receptors to bind to laminin. When the peptide was mixed with BL6 melanoma cells and injected intravenously into mice, the number of metastases from the BL6 cells was diminished (TABLE 1). Without being bound to any theory, it is believed that synthetic laminin receptor fragments compete with cells for immediate attachment to basement membranes and thus prevent metastatic cells from colonizing.

Based on the above, it is clear that the present invention can be used in a variety of ways in the diagnosis and therapy of cancer, as well as other diseases resulting from abnormal recognition of laminin by cells.

Specific examples to illustrate the present invention are now described.

EXAMPLE I

Identification of a Unique Human Placental Laminin Receptor Octapeptide

A. Materials and Methods

1. Tissue—Tissue from liver metastases derived from human breast and colon carcinoma were obtained from the Laboratory of Pathology, National Cancer Institute, and from the Department of Pathology, Glostrup Hospital, Copenhagen. Human placentae obtained from normal term deliveries were provided by the National Naval Medical Center, Bethesda, Md.

2. Purification of laminin receptor—Tumor tissue (100-300 g) or placental tissue (500 g) was homogenized in a Waring blender in vol (wt/vol) of phosphate buffered saline (137 mM NaCl/1.7 mM KCl/8.1 mM $Na_2HPO_4$/1.5 mM $KH_2PO_4$, pH 7.2). For this and subsequent buffers, the following protease inhibitors were added: 50 μg/ml phenylmethylsulfonyl fluoride, 5 mM benzamidine, 10 μg/ml aprotinin, 50 μg/ml soybean trypsin inhibitor, and 5 mM betahydroximercuribenzoate. After centrifugation at 500×g for 10 min, the homogenates were diluted 1:1 (vol/vol) in 0.3 M sucrose/25 mM Tris-HCl, pH 7.3, sonicated on ice with a Brinkman Polytron, centrifuged at 15,000×g for 20 min at 4° C., and finally the supernatant was ultracentrifuged at 143,000×g for 90 min at 4° C. The microsomal membranes in the resulting pellets were resuspended to 10 mg protein/ml in 25 mM Tris-HCl, pH 7.3/150 mM NaCl/1 mM $CaCl_2$/3 mM $MgCl_2$, and diluted into an equal volume of 1% octylphenorypolyethoxyethanol (Nonidet P-40, Sigma)/25 mM Tris-HCl, pH 7.2/150 mM NaCl/1 mM $CaCl_2$/3 mM $MgCl_2$, and extracted with end-over-end rotation at 4° C. for 6 hr. The preparation was ultracentrifuged at 200,000×g at 4° C. for 1 hr, and the supernatant was incubated for 16 hr at 4° C. with 2 ml of a Sepharose laminin affinity matrix which was prepared by coupling 2 mg laminin (purified as described by Timpl et al. (1979) *J. Biol. Chem.* 254: 9933-9937) per ml CBrN-activated Sepharose 4B (Pharmacia). The Sepharose-laminin matrix was then washed ten times in 25 mM Tris-HCl, pH 7.3/150 mM NaCl/1 mM $CaCl_2$/1 mM $MgCl_2$/0.05% Nonidet P-40 and once in the same buffer containing 400 mM NaCl. The laminin-Sepharose matrix was then packed into a 2 ml column. Protein fractions were eluted at room temperature with 1M NaCl/50 mM Tris-HCl, pH 7.3, immediately placed on ice, dialyzed against cold distilled $H_2O$, and concentrated by lyophilization.

3. Cyanogen bromide digestions and microsequencing—Purified laminin receptor was digested with cyanogen bromide as described by Ozols et al. (1977) *J. Biol. Chem.* 252: 5986-5989, dissolved in 400 μl of 0.1% trifluoroacetic acid/acetonitrile and run as two, 200 μl, injections on a reverse phase 25 cm×4.1 mm PRP-1 column (Hamilton) with a flow rate of 2 ml/min. Amino acid sequencing of cyanogen bromide-generated fragments was performed using a model 470A gas phase protein sequencer (Applied Bio Systems, Foster City, Calif.) with an attached model 120A PTH-analyzer using manufacturer's program 03RPTH.

4. Enzyme-linked immunoabsorbrnt assay (ELISA)—ELISAs were performed according to Engvall (1980) Methods Enzymol. 70: 419-439. Antibodies assayed included IgM mouse monoclonal antibody 2H5 (LR-1) against human laminin receptor as described by Liotta et al. (1985) *Exp. Cell Res.* 156: 117-126, rabbit anti-human albumin (Miles), and IgM mouse monoclonal antibody against α-amylase (obtained from R. Siraganian, National Institute of Dental Research). Bound antibodies were detected using peroxidase-conjugated rabbit-anti-mouse IgM (Kierkegaard and Perry Laboratories, Gaithersburg, Md.) or peroxidase-conjugated goat anti-rabbit IgG (Kierkegaard and Perry Laboratories).

5. Gel electrophoresis—Protein samples were analyzed by $NaDodSO_4$-polyacrylamide gel electrophoresis in the presence of dithiothreitol by the method of Laemmli (1970) *Nature (London)* 227: 680-685. Isoelectric focusing and two dimensional $NaDodSO_4$-polyacrylamide gel electrophoresis were carried out as described by O'Farrell (1975) *J. Biol. Chem.* 250: 4007-4021 and Wirth et al. (1986) Cancer Res. 46: 400-413. Immunoblotting was performed with anti-laminin receptor monoclonal antibody 2H5 as described by Liotta et al. (1985) supra.

B. Results

1. Purification of human laminin receptor—Isolation of preparative amounts of purified laminin receptor was accomplished by applying solubilized microsomal membrane-containing preparations from human metastatic breast and colon carcinomas and from human placental tissue to an affinity matrix of laminin-Sepharose 4B, followed by extensive washing of the affinity matrix, and elution of the receptor protein from the ligand by high salt (1M NaCl). When analyzed by $NaDodSO_4$-polyacrylamide gel electrophoresis (FIG. 1A), the purified protein from breast carcinoma and from colon carcinoma had an approximate apparent $M_r = 68,000$-72,000, as previously reported for human breast carcinoma laminin receptor isolated under less stringent conditions. The purification procedure resulted in a receptor protein yield of approximately 20 μg/100 g of tumor tissue and 2 μg/100 g of placental tissue (approximately 0.02% of the protein in the solubilized microsomal membrane preparations).

The purified laminin receptor preparations from breast carcinoma, colon carcinoma, and placenta were iodinated following standard procedures and analyzed by two dimensional gel electrophoresis to assess homogeneity of the preparations. A representative autoradiograph of tumor laminin receptor is shown in FIG. 1B. The apparent pI for laminin receptor was 6.4±0.2. Although FIG. 1B shows an elongated spot, other gels at different pH ranges and immunoblotting (as described by Liotta et al. (1985) supra) are consistent with a single polypeptide chain.

The purified laminin receptor preparations from the three sources were immobilized in microtiter wells and were reacted with a battery of antibodies to further demonstrate purity of the preparations and lack of contamination with laminin or albumin. In all cases, IgM mouse monoclonal antibody against the human laminin receptor, LR-1 (2H5), reacted positively, while rabbit anti-human albumin and a class matched IgM mouse monoclonal antibody directed against α-amylase, did not react. A representative ELISA is shown in FIG. 2.

2. Microsequence analysis of a cyanogen bromide peptide of placental laminin receptor—Repeated attempts to directly sequence the intact laminin receptor molecule were unsuccessful, presumably due to blocking of the amino terminus. Therefore, the receptor protein was cleaved with cyanogen bromide and the resulting peptides were fractionated by reverse phase HPLC. Microsequence analysis of a placental oligopeptide revealed an octapeptide with the sequence Met Leu Ala Arg Glu Val Leu Arg. A computer-assisted search for homologies (Wilbur and Lipman (1983) *Proc. Natl. Acad. Sci.* 80: 726-730) revealed that the octapeptide was unique.

EXAMPLE II

Isolation of Human Laminin Receptor cDNA Clones

A. Materials and Methods

1. Cell culture—Monolayer cultures of human umbilical vein endothelial cells were grown as described by Jaye et al. (1985) *Science* 228: 882-885.

2. Preparation of RNA—Total cellular RNA was extracted from cell layers in culture by the guanidinium isothiocyanate-cesium chloride density method described by Chirgwin et al. (1979) *Biochemistry* 18: 5294-5299. Poly (A)-containing RNA was isolated by chromatography on oligo(dT) cellulose (Type 3, Collaborative Research) according to the method of Aviv and Leder (1972) *Proc. Natl. Acad. Sci.* 69: 1408-1412.

3. Synthesis of cDNA—Oligo(dT)-selected human endothelial RNA was used as template for the synthesis of cDNA by the method of Buell et al. (1978) *J. Biol. Chem.* 253: 2471-2482 and double stranded cDNA was prepared as described by Wickens et al. (1978) *J. Biol. Chem.* 253: 2483-2495. The cDNA was made blunt ended with S1 nuclease as described by Ullrich et al. (1977) *Science* 196: 1313-1319 and subsequent treatment with the Klenow fragment of *E. coli* DNA polymerase I as described by Wartell and Resnikoff (1980) *Gene* 9: 309-319. The cDNA was then modified with EcoRI methylase, ligated to EcoRI linkers and exhaustively digested with EcoRI as described by Huynh et al. (1985) *DNA Cloning Volume* 1: a practical approach, ed., D. M. Glover, IRL Press Ltd, Oxford, England, pp. 49-78.

4. Construction and screening of human endothelial λgt11 cDNA library—EcoRI-linked cDNA was ligated to EcoRI-digested and phosphatase-treated λt11 as described by Huynh (1985) supra. The recombinant phage were packaged as described by Enquist and Sternberg (1979) *Methods Enzymol.* 68: 281-298 and amplified in *E. coli* Y1088 (ATCC 37195) as described by Huynh (1985) supra. *E. coli* Y1090 (ATCC 37197) cells were infected with the endothelial cell λgt11 cDNA library and 1.5 million plaques were screened by antibody recognition of a laminin receptor β-galactosidase fusion protein, as described by Young and Davis (1983) *Science* 222: 778-782, using anti-laminin receptor monoclonal antibody 2H5 (Liotta et al. (1985) *Exp. Cell Res.* 156: 117-126). This antibody recognizes or interferes with the ligand binding of the laminin receptor (Liotta et al. (1985) supra and Togo et al. (1985). *Basement Membranes*, ed. Shibata, S., Elsevier, New York, pp. 325-333). Antibody binding was detected using peroxidase-conjugated affinity-purified rabbit anti-mouse IgM as described supra in Example IA4. Positive plaques were identified, amplified, and rescreened to purity as described by Benton and Davis (1977) *Science* 196: 180-182. Filters containing plaques were reacted against control (as described in Example IA4 supra) as well as anti-rat laminin (Albrechtsen et al. (1981) *Cancer Res.* 41: 5076-5081).

5. Southern blot hybridization—Phage DNA was isolated as described by Maniatis et al. (1982) *Molecular Cloning: A Laboratory Manual*, Cold Spring Harbor Laboratory, Cold Spring Harbor, N.Y., pp. 77-85. Restriction endonuclease-digested DNAs were electrophoresed through agarose gels, transferred to nitrocellulose paper, and hybridized by the method of Southern (1979) *Methods Enzymol.* 68: 152-176. $^{32}$P-labeled probes were prepared by nick translation as described by Maniatis et al. (1975) *Proc. Natl. Acad. Sci.* 72: 1184-1188.

1 6. Subcloning and preparation of plasmids and cDNA insert—The EcoRI site linking the cDNA insert to the left arm of λgt11 was EcoRI site linking the cDNA insert to the left arm of λgt11 was missing in all six clones. A PvuII site 11 bp downstream was therefore utilized to purify cDNA insert from the largest recombinant phage λELR4. The EcoRI-PvuII restriction fragment of λELR4 was subcloned into the EcoRI-PvuII sites of pBR322 to make pLR4-1 and into the EcoRI-HincII polylinker sites of pUC8 to make pLR4-2. Subsequently, to facilitate cDNA sequencing away from the long poly(A) tail, the EcoRI-PstI restriction fragment of pLR4-1 was subcloned into the EcoRI-PstI sites of pBR322 to make pLR4-4. Recombinants of pBR322 were transformed into *E. coli* C600r$^-$m$^-$ (ATCC 33525) and pUC recombinants were transformed into *E. coli* JM 103 (Messing et al. (1981) *Nucleic Acids Res.* 9: 309-321) by the calcium chloride procedure of Mandel and Higa (1970) *J. Mol. Biol.* 53: 159-162. Supercoiled plasmid DNA was recovered by alkali lysis after equilibrium centrifugation in ethidium bromide-cesium chloride according to the procedure of Birnboim and Doly (1979) *Nucleic Acids Res.* 7: 1513-1523. cDNA inserts were isolated from restricted DNA and eluted from acrylamide gels as described by Sobel et al. (1978) *Proc. Natl. Acad. Sci.* 75: 5846-5850.

B. Results

1. Selection of laminin receptor cDNA by antibody recognition—The human endothelial cell λgt11 cDNA library was screened using anti-laminin receptor monoclonal antibody 2H5. As described in Materials and Methods supra, this antibody (a) specifically recognizes the laminin receptor on immunoblots, (b) recognizes the purified laminin receptor by ELISA (FIG. 2), (c) blocks the binding of laminin to either plasma membranes or cells, and (d) blocks attachment of cells to amnion basement membrane. These properties clearly indicate that the monoclonal antibody recognizes or interferes with the laminin binding domain of the laminin receptor. Six plaques were initially selected. After plaque purification, all six phage, designated λELR1-6, showed an intense reaction with the anti-laminin receptor monoclonal antibody, but showed no reactivity toward a class matched (IgM) monoclonal antibody directed against human α-amylase, nor toward antibodies directed against laminin or against proteins similar in size to laminin receptor such as albumin (FIG. 3).

2. Common domain of λELR1-6 - Restriction endonuclease digestion of the six phage, λELR1-6, revealed that the EcoRI site linking the 3' end of the cDNA insert to the left arm of λgt11 was missing in all six phage. Single, double, and triple endonuclease digestions using SacI, KpnI, HindIII and EcoRI were performed to map λELR1-6. These experiments, summarized in FIG. 4, indicated that (a) the sizes of the cDNA inserts ranged from about 450 to 975 bp, (b) all the clones shared an internal SacI site approximately 450-500 bp from the 3' end of the clones, (c) the insert of λELR6 extended only about 20 bp 5' to the internal SacI site, and (d) the inserts of λELR1 and λELR4 shared a HindIII site approximately 30 and 40 bp, respectively, from the 5' EcoRI site. The six recombinant phage thus have a common 450-500 bp region, extending from just 5' to the SacI site to the 3' end of each cDNA insert, suggesting that this region encodes the domain recognized by the monoclonal antibody 2H5. This observation was tested by Southern blot experiments in which KpnI-EcoRI and KpnI-SacI double digests of the DNA from each of the six recombinant phage were stringently hybridized to a PstI-SphI restriction fragment isolated from λELR4. A representative hybridization experiment, shown in FIG. 4, shows that a common 450-500 bp region of all 6 recombinant phage encodes the antigenic domain recognized by monoclonal antibody 2H5.

EXAMPLE III cDNA Sequence Determination

A. Materials and Methods

1. DNA sequencing—The cDNA from λELR4 was sequenced according to the strategy shown in FIG. 5. Both the chemical modification method of Gilbert and Maxam (1973) *Proc. Natl. Acad. Sci.* 70: 3581-3584 and the dideoxy synthesis method of Sanger et al. (1977) *Proc. Natl. Acad. Sci.* 74: 5463-5467 were used. In the former case, cDNA restriction fragments of subclones pLR4-1, pLR4-2, and pLR4-4 described in Example IIA6 supra were labeled either by treating the 5' end with T4 polynucleotide kinase (Boehringer-Mannheim) and ($\gamma$-P$^{32}$)ATP as described by Gilbert and Maxam (1973) supra or by tailing the 3' end with ($\alpha$-P$^{32}$) dideoxy ATP using a 3' tailing kit (Amersham). In the case of the dideoxy synthesis method, the EcoRI-SacI restriction fragment of λELR4 was subcloned into M13mp18 and M13mp19 (Yanisch-Perran et al. (1981) *Gene* 33: 103-119).

B. Results

1. Nucleotide and deduced amino acid sequence of the cDNA insert of λELR4—Sequence of the entire cDNA insert of λELR4 reveals a 253 amino acid open reading frame consistent with the right arm EcoRI insertion site of the λgt11 vector (FIG. 6). The sequence of the "common domain" recognized by the 2H5 epitope (see EXAMPLE IIB2 supra) extends from nucleotide 361 to nucleotide 765 in FIG. 6. It includes an octapentide-encoding sequence (nucleotides 409-432) identical to that of the purified cyanogen bromide-generated oligopeptide of placental laminin receptor described in EXAMPLE IB2 supra. Notable within this sequence is a six amino acid repeat separated by 3 amino acids toward the carboxy terminus of the laminin receptor. The cDNA sequences which encode the amino acid repeats are not identical (nucleotides 670-687 and 697-714). Following an ochre stop codon, the λELR4 cDNA insert includes a 3' untranslated region of 66 bp, including a canonical polyadenylation signal AATAAA 17 bp upstream from a long poly(A) stretch. After subtracting the length of the 3' untranslated region and the poly(A) tail, the largest possible extent of the 2H5 epitope, as defined by the common cDNA region of λELR1-6, can be narrowed down to 393 bp or 131 amino acids. Computer analysis by the method of Wilbur and Lipman (1983) *Proc. Natl. Acad. Sci.* 80: 726-730 reveals no significant homologies to known protein sequences.

It is noted that a potential membrane-spanning domain of the laminin receptor could include an eleven amino acid hydrophobic polypeptide encoded by nucleotides 52-84 of FIG. 6.

EXAMPLE IV

Antibody Recognition of cDNA-derived Synthetic Laminin Receptor Peptide

A. Materials and Methods

1. Preparation of antiserum13 Laminin receptor was purified from human metastatic breast carcinoma tissue as described in Example IA2 supra. Twenty μg of purified laminin receptor was electrophoresed through a NaDodSO$_4$-polyacrylamide gel as described in Example IA5 supra and cut out of the gel. Rabbits were immunized with the protein as described by Albrechtsen et al. (1981) *Cancer Res.* 41: 5076-5081. Serum was collected before antigen injections began (pre-immune serum) and at ten days after each booster injection.

2. ELISA—ELISAs were conducted as described in Example IA4 supra using pre-immune and immune serum obtained as described supra in Example IVA1.

3. Synthetic peptide RTLR2—A synthetic peptide, designated RTLR2, containing the sequence Pro-Thr-Glu-Asp-Trp-Ser-Ala-Gln-Pro-Ala-Thr-Glu-Asp-Trp-Ser-Ala-Ala-Pro-Thr-Ala was provided by Penninsula Laboratories, Inc. (Belmont, Calif.) following the standard methods well known in the art. This sequence was selected from nucleotides 667-726 in FIG. 6.

B. Results

1. Recognition of synthetic peptide by anti-laminin receptor antiserum—The nucleotide sequence 667-726 (FIG. 6) of the λELR4 cDNA was used to predict a peptide sequence. Synthetic peptide RTLR2 (EXAMPLE IVA3) was recognized in ELISA by rabbit antiserum directed against tumor laminin receptor but not by pre-immune serum (FIG. 7). This peptide includes two six amino acid repeats described in Example IIIB2 and has a predicted reverse turn configuration.

EXAMPLE V

Hybridization of Laminin Receptor cDNA to RNA

A. Materials and Methods

1. Cell lines—The MCF-7 human breast cancer cell line (parent) was provided by the Michigan Cancer Foundation. Two cloned MCF-7 cell lines MCF7-5H7 and MCF7-3E5, were obtained from P. Horan Hand (National Cancer Institute) and are described by Greiner et al. (1985) *Int. J. Cancer* 36: 159-166. The ZR-75 human breast carcinoma line is described by Engel and Young (1978) *Cancer Res.* 38: 4327-4339 and was obtained from L. Engel (National Cancer Institute) and the human renal carcinoma cell line A-704 was from S. Aaronson (National Cancer Institute) and is described by Giard et al. (1973) *J. Natl. Cancer Inst.* 51: 1417-1423. The human Panc-1 cell line was obtained from the American Type Culture Collection. Murine NIH-3T3 cells and its Kirsten virus-transformed derivative (KNIH) were obtained from M. Gottesman (National Cancer Institute) and their growth is described by Gottesman (1978) *Proc. Natl. Acad. Sci.* 75: 2767-2771. Murine F9 teratocarcinoma cells and their dibutyrylcyclic AMP plus retinoic acid differentiated derivatives (Strickland et al. (1980) *Cell* 21: 347-355) were from W. Anderson (National Cancer Institute). The rat L2 cell line is described by Wewer (1982) *Dev. Biol.* 93: 416-421.

2. Preparation of RNA—RNA was prepared from cell cultures as described in EXAMPLE IIA2 supra or by the guanidine-hydrochloride method described by Strohman et al. (1977) *Cell* 10: 265–273.

3. Northern hybridization—Five μg of total cellular RNA were separated on methylmercury/agarose gels and transferred to diazobenzyloxymethylcellulose paper (Schleicher and Schuell) by the method of Alwine et al. (1977) *Proc. Natl. Acad. Sci.* 74: 5350–5354 as described by Sobel et al. (1981) *Biochemistry* 20: 2678–2684. Filters were hybridized to nick translated cDNA insert as described in EXAMPLE IIA5 supra. Various time exposures of radioautographs were measured densitometrically to determine linear-response range. The blots were counterscreened with acting cDNA probe (described by Cleveland et al. (1980) *Cell* 20: 95–105) and with heat shock cDNa probe (described by Hickey et al. (1986) *Gene* 43: 147–154 to ensure equal amounts of RNA were transferred.

4. Laminin-binding assays—The number of laminin receptors per cell for each cell line was calculated from Scatchard plots of specifically bound ($^{125}$I)-labeled laminin to logarithmic growth phase cells as described by Liotta et al. (1985) *Exp. Cell Res.* 156: 117–126.

B. Results

1. Expression of human laminin receptor mRNA—It was previously reported that the amount and surface distribution of laminin receptor is different in various carcinomatous human tissues (Horan Hand et al. (1985) *Cancer Res.* 45: 2713–2719). In general, malignant tissues have more unoccupied laminin receptors on their cell surface and bind to more laminin than do their more benign counterparts. To determine if laminin receptor mRNA levels play a role in determining the amount of cell surface laminin receptors available for ligand binding, a Northern blot experiment was performed (FIG. 8). The laminin receptor cDNA insert recognizes a mRNA of about 1700 bases which is sufficient in length to encode a protein with the estimated size of laminin receptor. The level of hybridized RNA from a variety of human epithelial cell lines varied. In particular, there was greater hybridization to RNA from the metastatic breast carcinoma cell line MCF-7 than to RNA from the nonmetastatic breast carcinoma cell line ZR-75. In general, the level of hybridized RNA correlated directly with laminin binding assays (FIG. 9), suggesting that the amount of laminin receptor mRNA available for the biosynthesis of receptor may be a rate-limiting control step in the regulation of cellular attachment to laminin in the basement membrane. Hence, the determination of laminin receptor mRNA levels in human tumor tissue can be used diagnostically to predict the relative aggressiveness of the tumor or susceptibility to therapeutic regimens based on laminin receptor content. As mentioned above, this can be accomplished by Northern blot hybridization or in situ hybridization of sectioned tumor material, using laminin receptor cDNA as probe. Laminin receptor cDNA may be prepared as probe for the above mentioned procedures by a variety of means following standard techniques well known in the art. The nick translation procedure described in EXAMPLE IIA5 can be used to radiolabel cDNA insert with either ($^{32}$P), ($^{35}$S) or ($^{3}$H). Alternatively, the laminin receptor cDNA insert can be subcloned into plasmids permitting transcription of radiolabeled RNA by methods described by Melton et al. (1984) *Nucleic Acids Res.* 12: 7035–7056. Biotinylated RNA and DNA hybridization probes in conjunction with chromogenic detection systems have also been described, for example, by Langer et al. (1981) *Proc. Natl. Acad. Sci.* 78: 6633–6637 and by Leary et al. (1983) *Proc. Natl. Acad. Sci.* 80: 4045–4049.

2. Detection of laminin receptor mRNA in other species—Northern blots containing RNA from rat L2 cells and from murine cells such as NIH 3T3 and F9 teratocarcinoma and their derivatives also detected a mRNA of about 1700 bases. Thus, the human laminin receptor cDNA insert can cross hybridize to RNA from other vertebrate species (data not shown).

EXAMPLE VI

Polymorphisms of Laminin Receptor

A. Materials and Methods

1. Identification of cross-hybridizing laminin receptor cDNAs—The human endothelial cell λgt11 cDNA library described in EXAMPLE IIA4 was used to infect *E. coli* Y1088 cells (ATCC 37195) and screened using $^{32}$P-labeled cDNA insert from λELR4 by the plaque hybridization procedure of Benton and Davis (1977) *Science* 196: 180–182. Positive plaques were identified, amplified, and rescreened to purity as described by Benton and Davis (1977) supra.

2. DNA sequence determination—The cDNA inserts of positive phage were subcloned into the EcoRI site of pUC vectors as described in EXAMPLE IIA6, and cDNA sequence was determined by the method of Gilbert and Maxam (1973) *Proc. Natl. Acad. Sci.* 70: 3581–3584.

3. Isolation of human genomic DNA—Genomic DNA was isolated from human cell lines described in EXAMPLE VA1 supra by a gentle digestion with sodium dodecylsulfate and proteinase K as described by Blin et al. (1976) *Nucleic Acids Res.* 3: 2303–2308.

4. Southern hybridizations—Genomic DNA from the cell lines described above as well as from human liver (obtained from M. Young, National Institute of Dental Research) was digested exhaustively with EcoRI, HindIII, BamHI or XbaI, electrophoresed on agarose gels, transferred to nitrocellulose and hybridized to λELR4 cDNA insert as described in EXAMPLE IIA5 supra.

B. Results 1. cDNA sequence comparison—Partial cDNA sequences were determined for recombinant phage λELR10, λELR14, λELRI06, λELR112. The sequence from the 5' EcoRI site to the internal SacI site of λELR14 completely corresponds to nucleotides 7–381 of FIG. 6 and includes 96 additional bases upstream from λELR4. The other clones analyzed show high homology to λELR4 sequences but contain multiple point mutations. For each of the other clones, there are no open translational reading frames, suggesting that they may be cDNAs of pseudolaminin receptor genes.

2. Genomic DNA analysis—Southern blot analysis of high molecular weight genomic DNA from human liver and from a variety of human cell lines shows multiple hybridizing DNA bands. This suggests that there are multiple laminin receptor genes in the human genome, all of which cross-hybridize. In addition, multiple plaques, each containing unique DNA, were isolated by the plaque hybridization procedure described above from a λ Charon 4A library (obtained from T. Maniatis, Harvard University) of human genomic DNA partially digested with AluI/HaeIII. These findings suggest that the multiple cross-hybridizing laminin receptor genes are not identical. One possibility is that the human genome contains one active laminin receptor gene and several pseudogenes. The mRNAs transcribed from the pseudogenes are sufficiently stable to reach the cytoplasm and can be transcribed in vitro to make cDNA, and their corresponding cDNAs cross-hybridize with authentic laminin receptor cDNA such as λELR1-6 and can be used as alternative hybridization probes in Northern blots. However, due to multiple translational stop codons at the 5' ends of the pseudogenes, laminin receptor protein is not synthesized from them. It is necessary that all isolated laminin receptor cDNAs encode (in open reading frame) the amino acids predicted by λELR4 cDNA sequence to qualify is authentic laminin receptor cDNA.

EXAMPLE VII

Synthetic Laminin Receptor Peptides

A. Materials and Methods

1. Synthetic laminin receptor peptides—Synthetic peptide RTLR2-20 was derived from nucleotides 667–726 of FIG. 6 and is described in EXAMPLE IVA3 above. A control peptide in which the first proline is deleted and the threonine and glutamate residues are replaced by lysine and leucine, respectively, is designated RTLR2-control. Synthetic peptide RTLR3 contains the sequence Asn-Lys-Gly-Ala-His-Ser-Val-Gly-Leu-Met-Trp-Trp-Met-Leu-Ala-Arg-Glu-Val-Leu-Arg and was derived from nucleotides 373–432 in FIG. 6. Control peptides which do not contain predicted reverse turns were also synthesized. Control peptide RTC1 contains the sequence Ser-Ser-Gln-Asn-Ser-Ser-Gly-Ser-Glu-Ala-Ser-Glu-Thr-Pro-Val-Lys-Arg-Arg-Lys-Ser-Gly. Control peptide RTC2 contains the sequence Glu-Ser-Arg-Glu-Arg-His-Gly-Lys-Arg. Control peptide RTC3 contains the sequence Leu-Met-Trp-Trp-Met-Leu-Ala-Arg (derived from nucleotides 397–420 in FIG. 6). All synthetic peptides were purified by reverse phase HPLC as described in EXAMPLE IA3 and were provided by Penninsula Laboratories, Inc. (Belmont, Calif.) following the standard methods well known in the art.

Of course, the clone of the present invention can be employed to synthesize peptide(s) following standard techniques well known in the art. The λELR1-6 clones were selected by their ability to express hybrid β-galactosidase-laminin receptor peptides. The cDNA insert or fragments thereof may be subcloned into other vectors to produce other fusion proteins or nonfusion proteins as summarized, for example, by Maniatis et al. (1982) *Molecular Cloning: A Laboratory Manual*, Cold Spring Harbor Laboratory, Cold Spring Harbor, N.Y., pp. 404–430.

2. Binding assays—The ability of A2058 human melanoma cells, supplied by G. Todaro, National Cancer Institute, to bind specifically to laminin the presence of synthetic laminin receptor peptides was tested as described in EXAMPLE VA4.

Synthetic peptides RTLR2 and RTLR3 as well as control peptides were attached to solid support by incubation with p-nitrophenyl ester glass beads by the method of Brown et al. (1979) Biochemistry 18: 4901–4906. The beads were obtained from A. Day (Medical College of Virginia). The peptides were then incubated with ($I^{125}$) laminin and the amount of bound ($I^{125}$) laminin was determined.

3. Metastasis assays—Metastatic BL6 murine melanoma cells were obtained from Dr. I. Hart, Frederick Cancer Research Center, Frederick, Md. Freshly trypsinized cells were mixed with various concentrations of synthetic peptide RTLR2 (described above) and about $5 \times 10^4$ cells were injected intravenously (i.v.) in a volume of 0.1 ml per nude mouse by the method of Liotta et al. (1980) Nature 284: 682–688. There were 10 mice per group. Animals were sacrificed at 3½ weeks and the number of metastases were determined. Control synthetic peptides such as RTC1 of similar hydrophobic change had no effect on the number of metastases.

B. Results

1. Binding Studies—Synthetic peptides were produced based on the cDNA sequence (FIG. 6) and were used to study laminin receptor-ligand binding mechanisms. The presence of synthetic peptide RTLR2, but not its control counterpart (RTLR2-control) inhibited the ability of human A2058 melanoma cells to bind to laminin (FIG. 10). This suggests that at least one binding domain of the receptor for its ligand is contained within the RTLR2 sequence. Furthermore, when a variety of synthetic peptides were incubated with ($I^{125}$) laminin and the amount of labeled ligand able to bind was measured, the RTLR2 peptide had more binding activity than did RTLR3 or 3 other control peptides (FIG. 11). Such studies demonstrate that cDNA-derived laminin receptor peptides can be used to determine specific domains of the laminin receptor involved in various biological functions.

2. Metastasis—Synthetic peptides generated from the cDNA sequence can be used to inhibit cancer metastases. The number of metastases from BL6 melanoma cells was diminished when synthetic RTLR2 fragment was coinjected with the cells into mice (Table 1). Without being bound to any theory, it is postulated that the synthetic laminin receptor fragments compete with the cells for immediate attachment to basement membranes and thus prevent metastases from colonizing. Such results indicate that cDNA-generated synthetic laminin receptor fragments are useful in inhibiting metastases in cancer treatment.

TABLE 1

| Ability of synthetic laminin receptor peptide to inhibit BL6 melanoma metastases | |
|---|---|
| Amount of peptide injected | Mean # metastases |
| 0 | 41.3 ± 10.9 |
| 0.01 μg | 31.0 ± 14.4 |
| 0.1 μg | 31.8 ± 14.0 |
| 1.0 μg | 29.4 ± 10.8 |
| 10.0 μg | 7.9 ± 6.7 |
| | (Mann-Whitney U test $p < 0.001$) |

$5 \times 10^4$ BL6 melanoma cells were mixed with various concentrations of synthetic laminin receptor peptide RTLR2 and injected i.v. in a volume of 0.1 ml into each nude mouse (10 mice per group). Animals were sacrificed at 3½ weeks and the number of metastases in the lungs were determined.

It is understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A clone comprising a recombinant cDNA clone for encoding cell surface receptor for laminin having a nucleotide sequence as follows:

CGT GAT GGC ATC TAT ATC ATA AAT CTC
AAG AGG ACC TGG GAG AAG CTT CTG

CTG GCA GCT CGT GCA ATT GTT GCC ATT
GAA AAC CCT GCT GAT GTC AGT GTT ATA
TCC TCC AGG AAT ACT GGC CAG AGG GCT
GTG CTG AAG TTT GCT GCT GCC ACT GGA
GCC ACT CCA ATT GCT GGC CGC TTC ACT
CCT GGA ACC TTC ACT AAC CAG ATC CAG
GCA GCC TTC CGG AAG CCA CGG CTT CTT
GTG TTT ACT GAC CCC AGG GCT GAC CAC
CAG CCT CTC ACG GAG GCA TCT TAT GTT
AAC CTA CCT ACC ATT GCG CTG TGT AAC
ACA GAT TCT CCT CTG CGC TAT GTG GAC
ATT GCC ATC CCA TGC AAC AAC AAG
GGA GCT CAC TCA GTG GGT TTG ATG
TGG TGG ATG CTG GCT CGG GAA GTT
CTG CGC ATG CGT GGC ACC ATT TCC CGT
GAA CAC CCA TGG GAG GTC ATG CCT
GAT CTG TAC TTC TAC AGA GAT CCT GAA
GAG ATT GAA AAA GAA GAG CAG GCT
GCT GCT GAG AAG GCA GTG ACC AAG
GAG GAA TTT CAG GCT GAA TGG ACT
GCT CCC GCT CCT GAG TTC ACT GCT ACT
CAG CCT GAG GTT GCA GAC TGG TCT
GAA GGT GTA CAG GTG CCC TCT GTG CCT
ATT CAG CAA TTC CCT ACT GAA GAC TGG
AGC GCT CAG CCT GCC ACG GAA GAC
TGG TCT GCA GCT CCC ACT GCT CAG GCC
ACT GAA TGG GTA GGA GCA ACC ACT
GAC TGG TCT TAA GCT GTT CTT GCA TAG
GCT CTT AAG CAG CAT GGA AAA ATG
GTT GAT GGA AAA TAA ACA TCA GTT
TCT.

2. A probe obtained from the clone of claim 1 having the ability to hybridize to laminin receptor mRNA.

3. A method for diagnosing the aggressiveness of a carcinoma comprising reacting purified RNA from said carcinoma with the probe of claim 2, and determining the degree of hybridization between them, and comparing the degree of hybridization to a standard.

4. The method of claim 3 wherein said probe is radio-labelled.

5. The method of claim 3 wherein said probe is detected chromogenically.

6. A probe obtained from the clone of claim 1 having the ability to hybridize to a laminin receptor gene.

7. A method for diagnosing the aggressiveness of a carcinoma or the effectiveness of an agent for treating cancer cells comprising reacting a sample of a tissue suspected to have said cancer cells with the probe of claim 6, and determining the degree of hybridization between them, and comparing the degree of hybridization of a standard.

8. The method of claim 7 wherein said probe is radio-labelled.

9. The method of claim 7 wherein said probe is detected chromogenically.

10. A method for diagnosing the aggressiveness of a carcinoma or the effectiveness of an agent for treating cancer cells comprising reacting a sample of a tissue suspected to have said cancer cells with the probe of claim 1, and determining the degree of hybridization between them and comparing the degree of hybridization to a standard.

11. The method of claim 10 wherein said probe is radio-labelled.

12. The method of claim 10 wherein said probe is detected chromogenically.

13. A clone comprising a recombinant cDNA clone for encoding cell surface receptor for laminin contained in deposit ATCC 67199.

14. A probe obtained from the clone of claim 13 having the ability to hybridize to laminin receptor mRNA.

15. A method for diagnosing the aggressiveness of a carcinoma comprising reacting purified RNA from said carcinoma with the probe of claim 14 and determining the degree of hybridization between them, and comparing the degree of hybridization to a standard.

16. A probe obtained from the clone of claim 13 having the ability to hybridize to a laminin receptor gene.

17. A method for diagnosing the aggressiveness of a carcinoma or the effectiveness of an agent for treating cancer cells comprising reacting a sample of a tissue suspected to have said cancer cells with the probe of claim 16 and determining the degree of hybridization between them, and comparing the degree of hybridization of a standard.

18. A method for diagnosing the aggressiveness of a carcinoma or the effectiveness of an agent for treating cancer cells comprising reacting a sample of a tissue suspected to have said cancer cells with the probe of claim 16 and determining the degree of hybridization between them, and comparing the degree of hybridization to a standard.

19. The method of claim 18 wherein said probe is radio-labelled.

* * * * *